(12) United States Patent
Cobanoglu et al.

(10) Patent No.: US 10,433,782 B2
(45) Date of Patent: Oct. 8, 2019

(54) ELECTRONIC BUTTON FOR SMART GARMENTS

(71) Applicant: Sanko Tekstil Isletmeleri San. Ve Tic. A.S., Inegol—Bursa (TR)

(72) Inventors: Ozgur Cobanoglu, Inegol—Bursa (TR); Jitka Eryilmaz, Inegol—Bursa (TR); Ozgur Akdemir, Inegol—Bursa (TR)

(73) Assignee: Sanko Tekstil Isletmeleri San. Ve Tic. A.S., Inegol-Bursa (TR)

( * ) Notice: Subject to any disclaimer, the term of this patent is extended or adjusted under 35 U.S.C. 154(b) by 72 days.

(21) Appl. No.: 15/580,772

(22) PCT Filed: Jul. 29, 2016

(86) PCT No.: PCT/EP2016/068187
§ 371 (c)(1),
(2) Date: Dec. 8, 2017

(87) PCT Pub. No.: WO2017/017260
PCT Pub. Date: Feb. 2, 2017

(65) Prior Publication Data
US 2018/0220950 A1    Aug. 9, 2018

(30) Foreign Application Priority Data

Jul. 30, 2015 (EP) ..................... 15179147

(51) Int. Cl.
*H04W 4/70* (2018.01)
*A61B 5/00* (2006.01)
(Continued)

(52) U.S. Cl.
CPC ............ *A61B 5/4266* (2013.01); *A41D 1/005* (2013.01); *A44B 1/28* (2013.01); *A44B 1/34* (2013.01);
(Continued)

(58) Field of Classification Search
CPC ....................................................... H04W 4/70
See application file for complete search history.

(56) References Cited

U.S. PATENT DOCUMENTS

2006/0246744 A1* 11/2006 Marmaropoulos .... A41D 1/005
                                                                   439/37
2014/0187900 A1*  7/2014 Pernu ........................ A41F 1/00
                                                                   600/390

FOREIGN PATENT DOCUMENTS

DE    102006039587    2/2008
WO      2011093724    8/2011

OTHER PUBLICATIONS

International Search Report dated Oct. 13, 2016 for PCT/Ep2016/068187.

(Continued)

*Primary Examiner* — Ankur Jain
(74) *Attorney, Agent, or Firm* — Silvia Salvadori

(57) ABSTRACT

A system for transmitting signals from a garment to an analysis device, is provided. The system includes a button attachable to the garment by means of a pin passing through a hole arranged in a garment coupling portion to be clamped between a head of said pin and a button coupling surface. The button coupling surface includes an electric contact connected to at least one integrated circuit contained in the button for performing analog and digital processing of signals coming from at least one garment sensor. The button contains a wireless module for communicating data between the button and an analysis device. The garment coupling portion is provided with at least one conductive trace arranged on its surface and which faces the button coupling surface. The electric contact is arranged in order to contact at least one conductive trace.

21 Claims, 4 Drawing Sheets

(51) Int. Cl.
    *A44B 1/28*    (2006.01)
    *A41D 1/00*    (2018.01)
    *A44B 1/34*    (2006.01)
    *G08C 17/02*   (2006.01)
    *G06F 1/16*    (2006.01)
    *G08B 7/06*    (2006.01)
    *H02J 50/10*   (2016.01)
    *H02J 7/02*    (2016.01)

(52) U.S. Cl.
    CPC .......... *A61B 5/0002* (2013.01); *A61B 5/0015* (2013.01); *A61B 5/6804* (2013.01); *A61B 5/6805* (2013.01); *G08C 17/02* (2013.01); *H04W 4/70* (2018.02); *A61B 2562/0219* (2013.01); *A61B 2562/0261* (2013.01); *A61B 2562/227* (2013.01); *G06F 1/163* (2013.01); *G08B 7/06* (2013.01); *H02J 7/025* (2013.01); *H02J 50/10* (2016.02)

(56) References Cited

OTHER PUBLICATIONS

Search Report dated Jan. 20, 2016 for priority EP application No. 15179147.2.

* cited by examiner

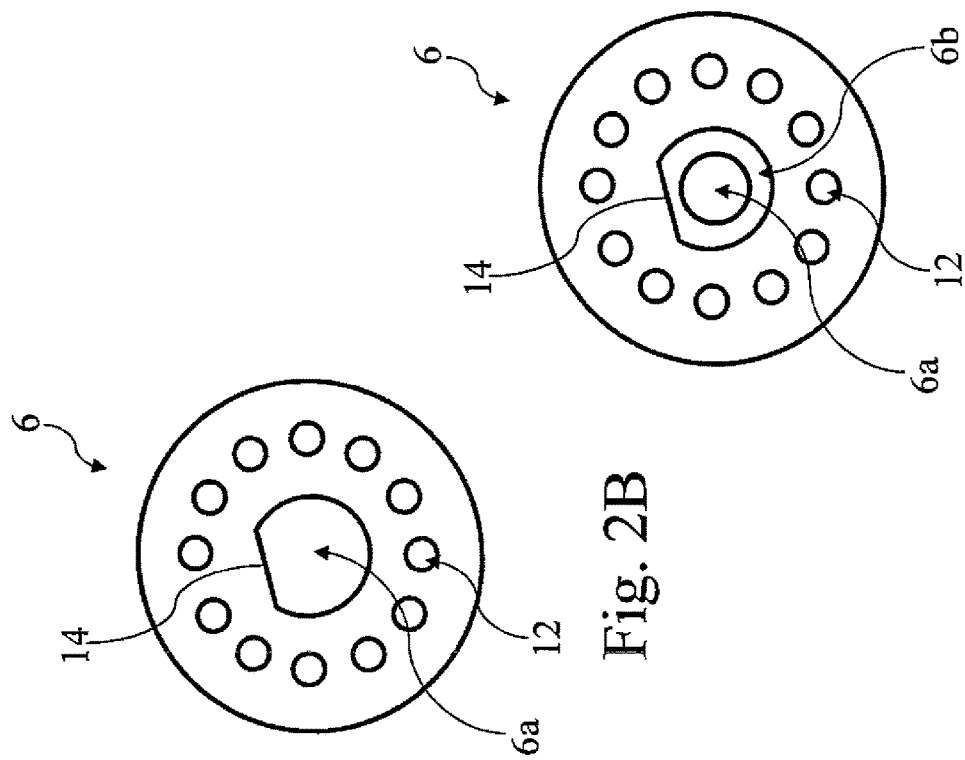
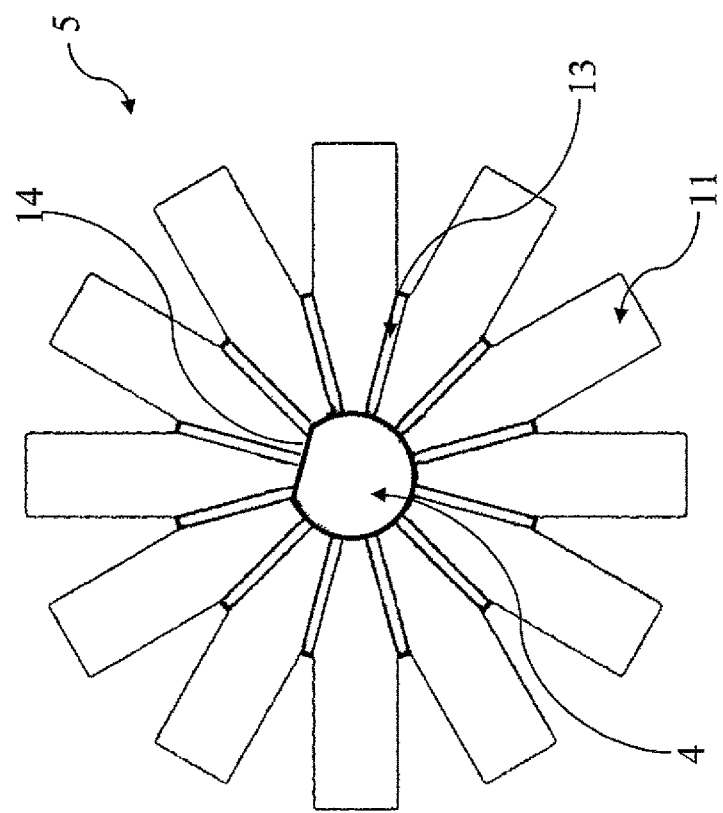

ELECTRONIC BUTTON FOR SMART GARMENTS

FIELD OF THE INVENTION

The present invention relates to the field of E-textiles (also known as "smart garments"). In particular, the present invention relates to a button (or in general a fastening element for garments) acting as a wearable electronic device for reading out signals coming from sensors embedded in a garment.

BACKGROUND OF THE INVENTION

Smart garments are generally provided with electronic components (e.g. sensors, actuators, microcontrollers, etc.) integrated in a fabric in order to provide articles of clothing (e.g. T-shirts, shoes, gloves, pants, etc.) used for different purposes, e.g. for monitoring the health of the wearer, for providing anti-theft functions, for monitoring the physical activity of the wearer, etc. Typically, signals coming from garment sensors (i.e. sensors embedded in the smart garment) travel along conductive yarns integrated into the fabric in order to reach one or more processing unit (e.g. a microcontroller) provided on the garment. Processing units are known, e.g. from DE102006039587, which are in the form of a button and are provided with electric contacts for receiving the signals coming from garment sensors. In particular, the processing units are usually firmly fixed to a portion of the garment; the electric contacts are configured to pierce and penetrate into the fabric and to contact the conductive yarns (e.g. by a clamping end) in the fabric.

Processing units may be provided with a sealing coating, covering the portion of garment to which the processing unit is fixed, for preventing infiltration of water, e.g. when the garment is washed. In some cases, the positioning and the coating of said processing units on the garment could be unaesthetic and/or uncomfortable for the wearer. Furthermore, in case of damage to a processing unit (that is the most delicate electronic component in a smart garment), the replacement of the damaged processing unit can be carried out only by a skilled labor.

SUMMARY OF THE INVENTION

An aim of the present invention is to overcome the drawbacks of the prior art solutions above cited and to provide a system for transmitting signals from a garment having sensors to an analysis device, which is not expensive, reliable and easy to maintain.

A further aim of the present invention is to provide a processing unit for the above mentioned system, which processing unit can be attached in a simple manner to several different garments for performing analog and digital processing of signals coming from different garment sensors embedded in the garments.

A further aim of the present invention is to provide a "smart" garment with a better aesthetic performance and a greater reliability with respect to the smart garments of the prior art.

These and other aims are reached by the present invention by means of a system according to claim 1 and the related dependent claims, by a processing unit according to claim 18 and the related claims, and by a garment according to claim 20 and the related dependent claims.

In particular, according to the present invention, the system for transmitting signals from a garment having at least one garment sensor to an analysis device, comprises a garment and a processing unit that is a button. The button is of the type attachable to a garment by means of a pin passing through a hole provided on the garment. The hole is arranged in a garment coupling portion that is the portion of garment to be clamped between the head of the pin and a button coupling surface (i.e. the surface of the button placed in contact with the garment coupling portion when the pin, passing through the hole of the garment coupling portion, is coupled with the button). For example, buttons having a pin and a socket for attaching the button to a garment are the so-called "denim buttons" i.e. the type of buttons typically used in jeans. Other similar types of pin+socket buttons are snap buttons, or in general fastening elements attachable to a garment by means of a pin passing through the garment (i.e. the fabric of the garment) in order to clamp a garment coupling portion between the button and the head of the pin.

According to an aspect of the present invention, the button contains at least one integrated circuit for performing analog and digital processing of signals coming from at least one garment sensor and a wireless module for communicating data between the button and an analysis device (e.g. PC, smartphone, etc.).

The garment coupling portion, that will be discussed with more details later, is provided with at least one conductive trace connected to the garment sensor(s). Conductive traces are configured to provide signals coming from the garment sensors on the surface of the garment coupling portion. In other words, an external surface of the garment coupling portion is provided with one or more conductive traces arranged to provide signals coming from the garment sensor(s).

According to a particular aspect of the present invention, the button coupling surface is provided with at least one electric contact connected to the integrated circuit contained into the button. The electric contacts are arranged in order to contact conductive traces on the surface of said garment coupling portion. Thank to this, the button can be attached to a garment and detached from it, in a simple manner because electric contacts and conductive traces work only by contact without any direct constraint between them. In other words, the electric contacts are arranged and configured in order to avoid piercing the garment coupling portion when the button is attached to the garment.

The button of the present invention is of the type that can be removed from the garment; preferably the button is a button in which the pin is fixed to the socket of the button by a reversible snap connection. The button is dimensioned to assure a contact between the surface of the coupling portion of the button with the surface of the coupling portion of the garment, so that the electric contacts of the button and the conductive traces on the garment are electrically connected. Thus, when the pin is detached from the button, the button is free to be removed from the garment.

According to another aspect of the present invention, the electric contacts are substantially flush with the button coupling surface. With "substantially flush" it is meant that the electric contacts can extend slightly outside or inside from the button coupling surface. Preferably, the electric contacts are provided with an electric contact coupling surface substantially flat. The electric contact coupling surface can be defined as the surface of the electric contacts placed in contact with the conductive traces of the garment coupling portion when the pin, passing through the hole of the garment coupling portion, is coupled with the button). In other words, the external surface of the electric contacts is substantially flat. In this way, a proper contact between conductive traces and electric contacts can be secured preventing damages to the garment coupling portion. In other words, when the garment coupling portion is clamped between the button coupling surface and the head of the pin, electric contacts do not damage the conductive traces.

According to another aspect of the present invention, the button coupling surface comprises a socket for the engagement of the pin into the button. A plurality of said electric contacts are arranged around the socket on said button coupling surface. Conductive traces are arranged around the hole of the garment coupling portion and the pin acts as a guide to maintain the hole of the garment coupling portion coaxially with the socket of the button coupling surface.

According to an aspect of the present invention, the button comprises a battery for power supplying the integrated circuit and the wireless module contained into the button. The battery can be detachable from the button or contained within the button. In this latest case the battery is preferably rechargeable, more preferably by an inductive coupling.

According to another aspect of the present invention, the button can contain at least one button sensor connected to the integrated circuit of the button. The button sensor can comprise e.g. an accelerometer and/or a gyroscope, for measuring e.g. the physical activity of the wearer.

According to a particular aspect of the present invention, the integrated circuit comprises at least one analog front-end circuit with one or more input stages for performing analog processing of the signals coming from the garment sensors and/or from the button sensors. Each input stage is preferably designed in function of the type of the sensor and of the related signal to be processed.

Preferably, the integrated circuit comprises at least one A/D converter and a microcontroller. The A/D converter digitizes the signals processed by the analog front-end circuit, so that the microcontroller can perform digital processing of the digitized signals. Furthermore, microcontroller executes a communication protocol between the wireless module and the analysis device. In this way data collected by the buttons can be provided to the analysis device by a wireless connection (e.g. Wi-Fi, Bluetooth, NFC, etc.). The analysis device (e.g. PC, smartphone, etc.) is preferably provided with a dedicated software for carrying out different type of analysis in function of the data provided by the button, i.e. in function of the type of sensors embedded in the garment.

In particular, a further object of the present invention is a garment comprising a garment coupling portion for the attachment of a button according to an embodiment of the present invention. The garment coupling portion is provided with at least one conductive trace connected to at least one garment sensor provided in the garment.

According to an aspect of the present invention, the conductive traces are arranged on the surface of the garment coupling portion, in order to be faced to the button coupling surface of the button according to the present invention. As mentioned above the button coupling surface is provided with electric contacts for reading out the signals coming from the garment sensor. The electric contacts and the conductive traces are arranged to be put in contact to each other when the button is attached to the garment.

According to a particular aspect of the present invention, said at least one conducting trace is made of an anti-corrosion material. For example said anti-corrosion material can be embroidered steel yarns or a thermoplastic material. Thank to this, conductive traces can provide a protection for the electric contact of the button that can be made of an ordinary conducting metal. In particular, conductive traces are preferably made of a soft material configured for covering the electric contacts of the button when the button is attached to the garment. In this way, electric contacts are sealed from water and the garment can be washed with the button attached to it.

The conducting traces are preferably arranged radially around the hole provided in the garment coupling portion. In this way conductive traces can be aligned with the electric contacts of the button. In particular, as mentioned above, electric contacts are arranged around the socket of the button coupling surface so that the pin works as a guide allowing to maintain the hole of the garment coupling portion coaxially with the socket of the button coupling surface.

In a preferred embodiment, the pin, the hole and the socket are shaped in a such manner that only an univocal alignment is possible between the electric contacts of the button and conductive traces of the garment. In other words, the pin, the hole in the garment and the socket are shaped in a such manner that when the pin is coupled in the hole and/or in the socket, the pin cannot be rotated (i.e. the pin is constrained in rotation).

Preferably, the garment coupling portion comprises an insulating material arranged between the conductive traces. In this way, the number of conductive traces (and consequently the number of the related electric contacts of the button) can be maximized, preventing short-circuits between conductive traces. In particular, when the garment coupling portion is clamped between the head of the pin and the button coupling surface, conductive traces could be deformed by the electric contacts pressure. If the conductive traces are not properly spaced to each other, a short-circuit could be caused by said deformation. The insulating material arranged between the conductive traces prevents an electric contact between them especially in the case of conductive traces made of soft material. Thank to this the spacing between conductive traces can be minimized.

According to another aspect of the present invention the garment sensors embedded in the garment can comprise a plurality of electrodes for measuring vital signals, or at least one strain sensor, or at least one sweat sensor or any combination of the preceding.

With the term "vital signal" it is meant a signal related to an activity and/or a parameter of the human body. For example vital signals can be the skin surface potentials which can be generated by muscular activity, neuron activity, heart activity, etc. In this case the measurement of said vital signals can be considered as a passive measurement, i.e. vital signals are produced by the human body and the electrodes (garment sensors) provided in the garment are used only to receive said signals.

According to another aspect of the present invention, electrodes can be used for driving a reference signal through the human body and for receiving a back signal that is the reference signal distorted by the passage through the human body (e.g. a distortion of the reference signal can depend on the water/fat of the tissue through which the reference signal is passed). In this latest case the measurement of the vital signals can be considered as an active measurement, i.e. an electric signal (the reference signal) is produced by an external device (i.e. the button) and it is driven through the skin of the wearer, thus by analyzing the difference between the reference signal and the back signal, parameters related to the human body, such as the body fat index, can be determined.

Thanks to the present invention, processing units of a smart garments can be packaged in a sealed manner as a fastening element for garments. The packaging in form of a button allows to improve the aesthetic performance of the garment. Furthermore thanks to the particular coupling between electric contacts of the button and conductive traces of the garment, the button can be attached to the garment and detached from it, in a simple manner. For example, the user can detach in a simple manner the button from the garment for recharging the battery and attach to the garment another button previously recharged. A first benefit of the present invention is that the user can attach the same button to several garments e.g. garments provided with different garment sensors. Analogously the same garment can be used with several buttons e.g. the user can replace a button with another on the basis of his aesthetics.

Another benefit of the present invention is that, in case of damage to an electric component of the button, the replacement of the button can be carried out in a simple manner by the user, so that the smart garment can be put back into operation quickly without the need of a skilled labor.

BRIEF DESCRIPTION OF THE DRAWINGS

Further aspects and advantages of the present invention will be discussed more in detail with reference to the enclosed drawings, given by way of non-limiting example, wherein:

FIG. 2A is a plant view of the garment coupling portion in a particular embodiment of the present invention;

FIG. 2B is a plant view of the button coupling surface in a particular embodiment of the present invention;

FIG. 2C is a plant view of the button coupling surface of a further embodiment of the present invention;

EMBODIMENTS OF THE INVENTION

Figure 1:
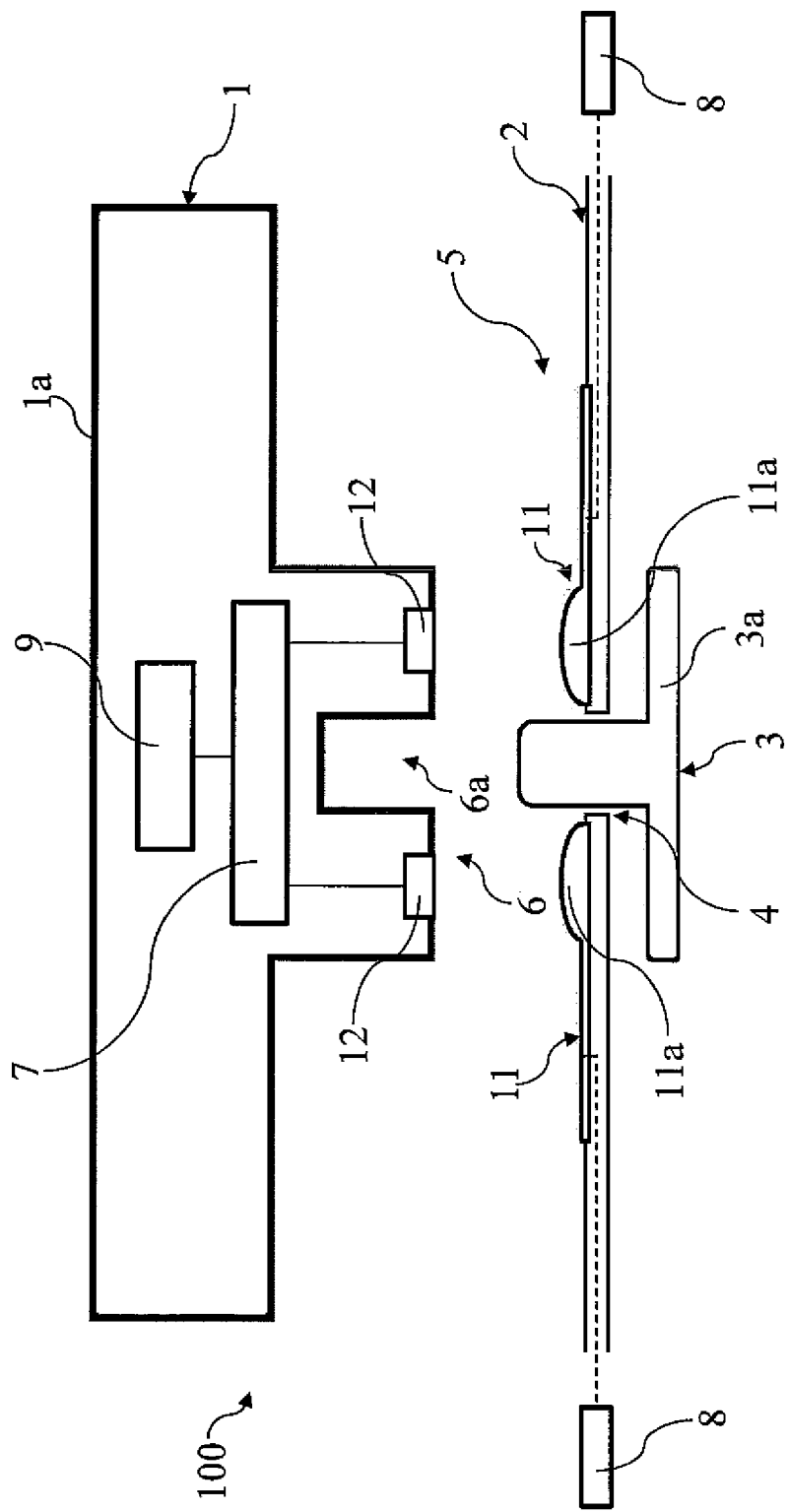
FIG. 1 is a side view of the button and the garment according to an embodiment of the present invention.

FIG. 1 shows a system 100 for transmitting signals from a garment 2 having at least one garment sensor 8 to an analysis device 10. The system 100 comprises a garment 2 and a processing unit that is in the form of a button 1. The button 1 comprises a shell 1a conformed to act as a fastening element for a garment 2. In particular, the embodiment shown in FIG. 1 is similar to a denim button, i.e. a button for jeans. Other embodiments can provide for example a button comprising a shell 1a conformed as a male or female part of a snap fastener, also called snap button, of the type known for use e.g. in a jacket, a shirt, and similar garments.

The button 1 is of the type attachable to a garment 2 by means of a pin 3 passing through a hole 4 provided on the garment 2. The hole 4 is arranged in a garment coupling portion 5 that is a portion of garment to be clamped between the head 3a of the pin 3 and a button coupling surface 6.

In particular, the button coupling surface 6 is provided with a socket 6a for the engagement of the pin 3, thus when the pin 3 is engaged into the socket 6a the garment coupling portion 5 is clamped between the head 3a of the pin 3 and the button coupling surface 6. In a possible embodiment, the pin 3 and the socket 6a may be provided with a snap connection; in other embodiments, pin and socket are provided with a thread connection for screwing the pin 3 in the socket 6a.

The button 1 contains at least one integrated circuit 7 for performing analog and digital processing of signals coming from at least one garment sensor 8 embedded in the garment 2, and a wireless module 9 for communicating data between the button 1 and an analysis device 10. The wireless module 9 can comprise for example a Wi-Fi module and/or a Bluetooth module and/or a NFC module (Near Field Communication).

As it will discussed with more details later, signals coming from the garment sensors 8 are processed by the integrated circuit 7 in order to provide data to be transmitted by the wireless module 9 to the analysis device 10 that can be e.g. a PC, a smartphone or in general an electronic device for receiving data from the button 1 and for providing a result to the user. For example the analysis device 10 can be used for showing the data collected by the button 1 (e.g. by means of a screen) and/or for carrying out an algorithm for calculating one or more parameters or indexes associated to the garment 2 and/or associated to the wearer.

The garment 2 can be provided with one or more garment sensors 8 such as electrodes, strain sensors, swat sensors, etc., integrated in the garment in a known manner. For example electrodes can be deposited in a fabric (e.g. a denim fabric) by means of a screen printing process, or a knife coating process, or by means of other process known in the art. Said electrodes can be arranged in the garment 2 for monitoring vital signals such as EMG (electromyography), ECG (electrocardiography), GSR (galvanic skin response), as well as BFI (body fat index), etc.

As shown in FIG. 1, the garment coupling portion 5 is provided with conductive traces 11 connected to the garment sensors 8. The electric connection between garment sensors 8 and conductive traces 11 is indicated symbolically by a dotted line. For example, garment sensors 8 and conductive traces 11 can be electrically connected by means of conductive yarns (e.g. metal fibers), arranged along a path in the garment 2. This solution is useful e.g. when the garment sensors 8 are distanced from the garment coupling portion 5. In this case, the electric signals coming from the garment sensors 8 travel along the conductive yarns and reach the conductive traces 11 of the garment coupling portion 5.

In the case of garment sensors 8 placed in proximity of the garment coupling portion 5, conductive traces 11 can be directly connected to the garment sensors 8. Preferably, the conductive traces 11 are connected to conductive yarns or to garment sensors 8 by means of a conductive paste.

In general, electric signals coming from garment sensors 8 reach the conductive traces 11 for being available on the surface of the garment coupling portion 5.

For reading out the signals coming from the garment sensors 8, the button coupling surface 5 is provided with at least one electric contact 12 connected to the integrated circuit 7. Electric contacts 12 are arranged in order to contact the conductive traces 11 on the surface of the garment coupling portion 5.

As shown in FIG. 1, when the garment coupling portion 5 is clamped between the head 3a of the pin 3 and the button coupling surface 6, electric contacts 12 and conductive traces 11 are in contact with each other, thus the signals coming from garment sensors 8 can be provided to the integrated circuit 7 of the button 1.

Preferably, electric contacts 12 are substantially flush with the button coupling surface 6 of the button (i.e. that electric contacts 12 extend slightly outside or inside from the button coupling surface 6), so that when the button 1 is attached to the garment 2, electric contacts 12 press against conductive traces 11 without pierce them.

Preferably, conductive traces 11 are shaped with a bump 11a, i.e. a portion of conductive trace 11 having greater thickness, to be pressed by the electric contacts 12 of the button 1. The bump 11a allows to reinforce the portion of conductive trace subjected to the pressure of the electric contacts 12 when the garment coupling portion 5 is clamped between the head 3a of the pin 3 and the button coupling surface 6.

FIGS. 2A and 2B show respectively a garment coupling portion 5 and a button coupling surface 6 of a particular embodiment of the present invention. In particular, FIG. 2A is a plant view of a garment coupling portion 5 provided with twelve conductive traces 11, preferably arranged radially around the hole 4 of the garment coupling portion 5. Further embodiments can provide a garment coupling portion 5 having a different number of conductive traces 11, or wherein conductive traces 11 are arranged along directions different from the radially direction shown in FIG. 2A.

The radial arrangement of conductive traces 11 along their main direction of extension around the hole 4 of the garment coupling portion 5 allows to maximize the number of conductive traces 11 on a determined area of the garment coupling portion 5. Preferably, the conducting traces are provided with a portion tapered towards the hole for further maximizing the number of conductive traces 11.

In FIG. 2A, conductive traces 11 are arranged uniformly around the hole 4 of the garment coupling portion (i.e. all the conductive traces 11 are equally spaced with each other). Further embodiment can provide a garment coupling portion 5 with conductive traces 11 arranged radially around the hole 4 of the garment, but distributed differently. For example, an embodiment (not shown) can provide that the garment coupling portion 5 is provided with ten conductive traces 11 obtained by removing two conductive traces from the embodiment of FIG. 2A. In this case the conductive traces 11 will be distributed on one or two circular sectors around the hole 4. For example, another embodiment (not shown) can be provided with conductive traces 11 arranged radially around the hole 4 and distributed in two or more circular sectors each having a determined angular amplitude (wherein each circular sector comprises a determined number of conductive traces 11). In general the number of conductive traces 11 of the garment coupling portion 5 depends on the number and on the type of garment sensors 8 embedded in the garment 2.

Preferably, the garment coupling portion 5 comprises an insulating material 13 arranged between the conductive traces 11. The insulating material 13 prevents short-circuits between conductive traces 11, that could be caused by a deformation of conductive trace 11 due to the pressure of the electric contacts 12 (e.g. when the spacing of the conductive traces 11 is reduced). Conductive traces 11 are preferably made of an anti-corrosion material. For example conductive traces 11 can be made of embroidered steel yarns or a thermoplastic material. Thank to this, conductive traces 11 can provide a protection for the electric contacts 12 that can be made of an ordinary conducting metal. In particular, conductive traces 11 are preferably made of soft material for sealing electric contacts from water. In this way, when the button 1 is attached to the garment 2, electric contacts 12 are covered by conductive traces in a sealing manner and the garment 2 can be washed with the button 1 attached to it.

In FIG. 2B is shown the button coupling surface 6 of a button 1 according to an embodiment of the present invention. In the embodiment shown in FIG. 2B, the button coupling surface 6 is provided with twelve electric contacts 12 arranged around the socket 6a of the button 1, preferably along a circular path. Electric contacts 12 are arranged to be put in contact to the conductive traces 11 of the garment coupling portion 5 shown in the embodiment of FIG. 2A.

However, further embodiment can provide a button 1 having a button coupling surface 6 with a different number of electric contacts 12, or arranged in a different manner with respect to the circular arrangement shown in FIG. 2B (analogously to what mentioned above about to the garment coupling portion).

In general, conductive traces 11 and electric contacts 12 are arranged respectively on the garment coupling portion 5 and on the button coupling surface 6 in order to be put in contact with each other. In particular, for each conductive trace 11, there is one electric contact 12 to be put in contact with it. Thus, the number of electric contacts 12 can be equal or greater than the number or conductive traces 11 provided on the garment coupling portion 5. For example, in the case of two garments, wherein a first garment is provided with a first type of garment sensors 8 (e.g. only strain sensors), and the second garment is provided with a second type of sensor garments (e.g. only electrodes for EMG) then, the garment coupling portions of the two garments can be provided with conductive traces 11 arranged in a such manner that the same button 1 can be used in both the two garments.

In other words, electric contacts 12 and conductive traces 11 are preferably arranged according to one or more standard arrangements. Each standard arrangement is determined in function of the number and the type of garment sensors provided in the garment.

For example, garments having a determined number and a determined type of garment sensors 8, will be provided with conductive traces arranged according to a particular standard arrangement. Said garments can be used with a particular type of button 1 provided with electric contacts arranged according the same standard arrangement. The button is preferably provided with a number of electric contacts equal to the maximum number of conductive traces that can be provided on the garments. Furthermore, each electric contact 12 is connected to the integrated circuit 7 for performing a particular analog and digital processing of the signal coming from a determined type of garment sensor 8. Thus, each standard arrangement provides that for each conductive trace 11 is associated a determined electric contact 12 arranged on the button coupling surface 5 in order to obtain an univocal correspondence between conductive traces 11 and electric contacts 12.

Preferably, the pin 3, the socket 6a and the hole 4 are shaped in a such manner that only an univocal alignment is possible between the electric contacts 12 of the button 1 and conductive traces 11 of the garment 2. In this way the user can attach easily and correctly the button to the garment.

In particular, the embodiment shown in FIGS. 2A and 2B is provided with a pin 3, a socket 6a and a hole 4 having a symmetry breaking reference 14 (i.e. an asymmetric reference portion 14) obtained as a "cut" along a side of the pin section. In this way the pin 3 works as a guide allowing to maintain the hole 4 of the garment coupling portion 5 coaxially with the socket 6a of the button coupling surface 6. As result, electric contacts 12 are maintained aligned with conductive traces 11 during the engagement of the pin 3 in the socket 6a of the button 1.

In another embodiment, the pin and the socket are provided with a thread to attach the pin to the button. In this case the pin 3 has to be rotated into the socket, pin 3 and socket 6a thus preferably have a circular section; in this embodiment, shown in FIG. 2C, a portion 6b of the button is protruding from the coupling surface 6 of the button and it is shaped to conform to the asymmetric shape 14 of the hole in the garment. In other words, in this embodiment the hole 4 houses and is engaged by a portion of the button; portion 6b preferably is arranged around socket 6a.

In some embodiment, the pin, the socket and the hole are shaped in order to distinguish different type of buttons and garments, i.e. in order to distinguish different standard arrangements mentioned above.

Figure 3:
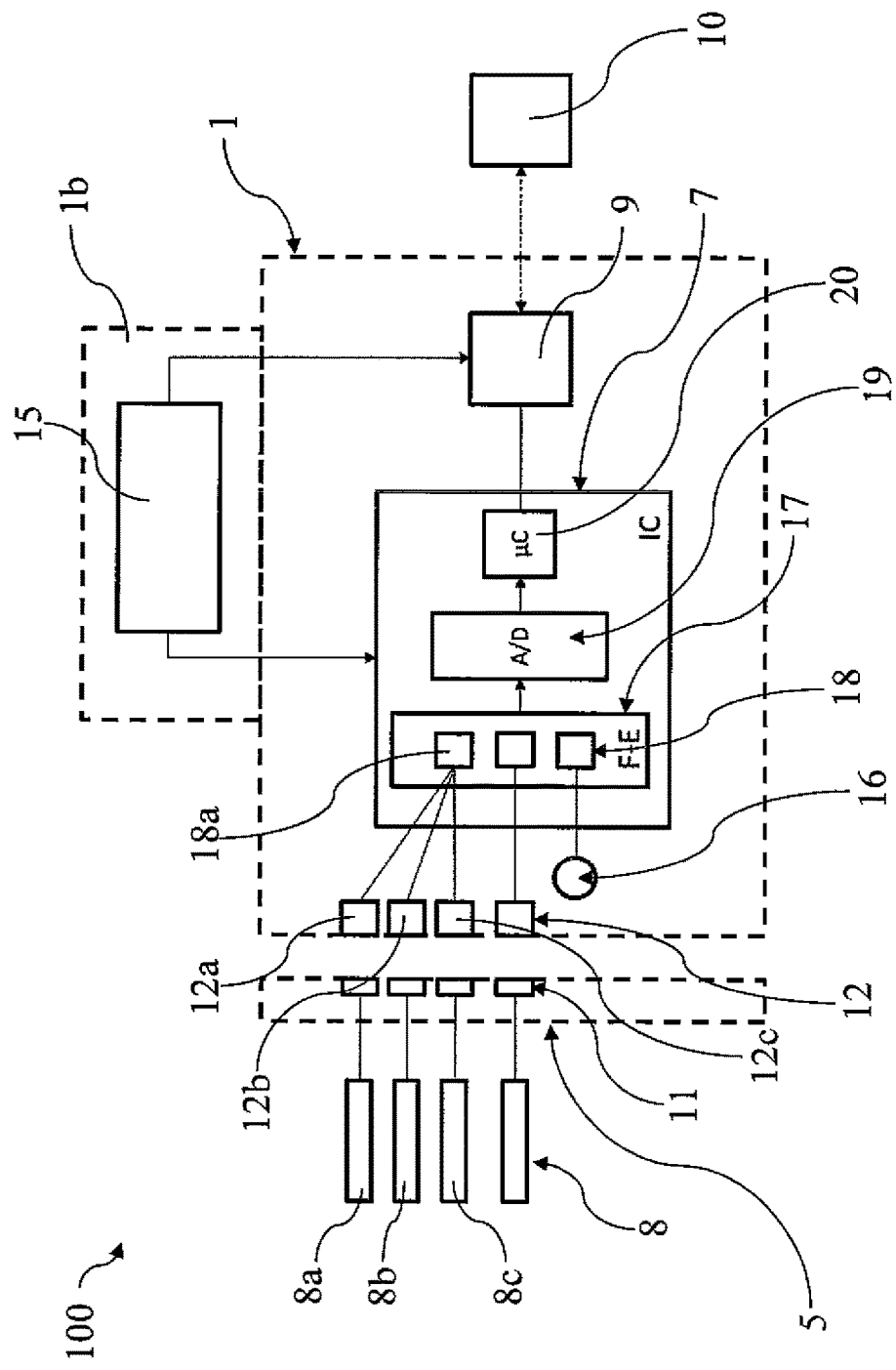
FIG. 3 is a block scheme of a possible architecture of the button according to an embodiment of the present invention.

FIG. 3 shows a block scheme of a possible architecture of the system 100 according to the present invention. In this scheme the button 1 comprises an integrated circuit 7 and a wireless module 9 power supplied by a battery 15. The battery 15 is preferably contained in a housing 1b of the button 1. In particular, an embodiment of the invention can provide that the battery 15 is detachable from the button 1, by removing the battery 15 from the housing 1b. In this case the battery 15 can be for example a rs2032. Another embodiment can provide that the housing 1b for the battery 15 is contained in a sealed manner into the button 1 (i.e. the battery is contained within the button 1). In this latest case the battery 15 is preferably rechargeable, more preferably by means of an inductive coupling.

As shown in FIG. 3, the button 1 contains at least one button sensor 16 connected to the integrated circuit 7 of the button 1. The button sensor 16 can comprise e.g. an accelerometer and/or a gyroscope, for measuring e.g. the physical activity of the wearer.

The integrated circuit 7 comprises at least one analog front-end circuit 17 with one or more input stages 18 for performing analog processing of the signals coming from garment sensors 8 and/or from the button sensor(s) 16. In particular, the electric signals coming from the garment sensors 8 are provided to the input stages by electric contacts 12 that are connected to input stages 18. Button sensors 16 (contained into the button) are connected directly to the input stages 18.

The integrated circuit 7 comprises at least one A/D converter 19 for digitizing the signals processed by the analog front-end circuit 17 and a microcontroller 20 for performing digital processing of digitized signals and for executing a communication protocol between the wireless module 9 and the analysis device 10. Preferably the integrated circuit 7 is provided with an A/D converter 19 for each input stage 18. In FIG. 3, all A/D converters 19 are indicated symbolically by an A/D conversion block connected to the analog front-end circuit 17.

The electrical signals digitized by the A/D converter 19 are thus provided to the microcontroller which performs a digital processing of the signal, e.g. digital filtering, calculating of parameters, checking of the garment sensors connected to the button, detecting the charging state of the battery, etc., and provides to the wireless module 9 a data package to be transmitted to the analysis device 10.

As mentioned above, each input stage 18 is designed for processing signals coming from a particular garment sensor 8 or button sensor 16. For example in the scheme shown in FIG. 3, three electric contacts 12a, 12b, 12c are connected to an input stage 18a. In this example said input stage 18a can be designed e.g. for processing EMG signals coming from three electrodes 8a, 8b, 8c embedded in the garment.

Figure 4:
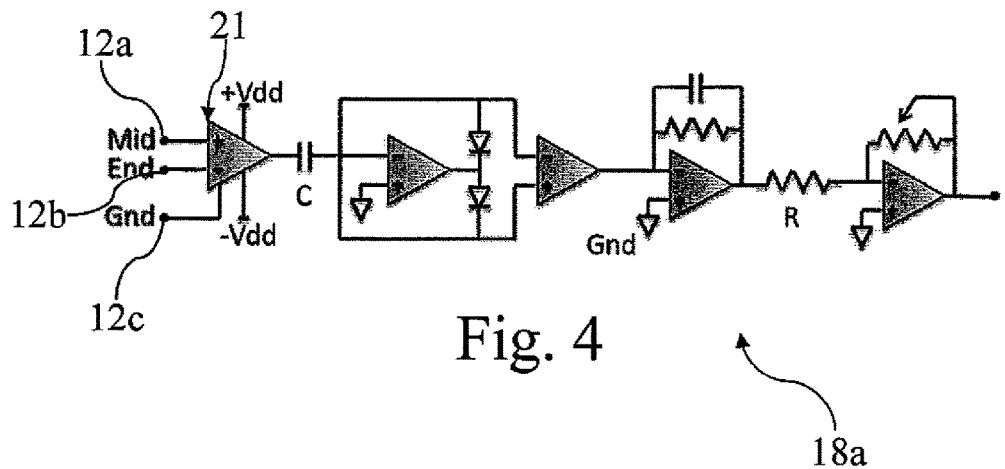
FIG. 4-6 are circuitry schemes of some possible input stages of the button according to an embodiment of the present invention.

In FIG. 4 it is shown a possible circuitry scheme of the input stage 18a for processing an EMG signal. In particular, three input signals (Mid, End, Gnd) coming from three respective electrodes 8a-8c are inputted to a first operational amplifier 21. This first operational amplifier 21 amplifies the difference between two signal (Mid-End) with respect to a third signal (Gnd). The signal is then rectified, integrated and amplified with an adjustable gain to be provided to an A/D converter.

Figure 5:
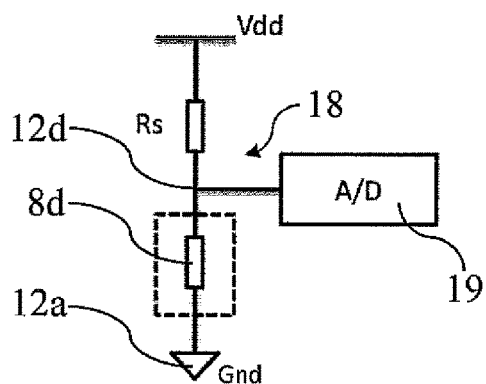

FIG. 5 shows the circuitry scheme of another input stage 18. In this example the input stage 18 is a voltage divider for processing a signal coming from a strain sensor 8d. In this case, the garment sensor 8 can be a resistive sensor (e.g. a flexible resistor) connected between two conductive traces. By means of two electric contacts 12d, 12e, the strain sensor 8d is connected to the input stage 18. An electric contact 12d is connected to a ground node and the other electric contact 12e is connected to an intermediate node of the voltage divider.

Figure 6:
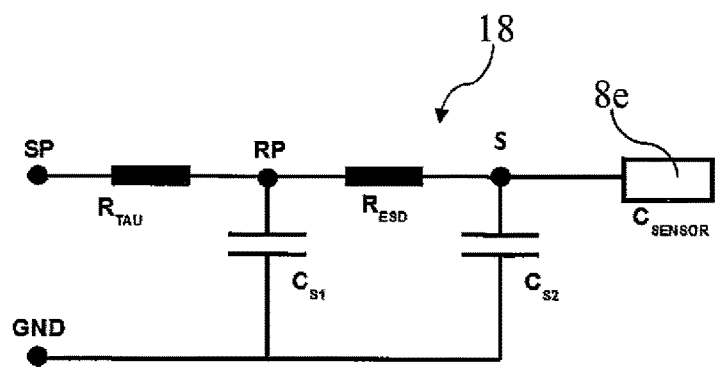

FIG. 6 is a circuitry scheme of an input stage 18 for processing signals coming from capacitive sensors 8b. In this example the input stage 18 comprises an input terminal S, for receiving a signal coming from a capacitive sensor 8b embedded in the garment 2, and a ground terminal (GND). These two terminals are connected to electric contacts 12. The input stage 18 comprises further two terminals SP, RP connected preferably to the microcontroller 20. In this case no A/D converter is used for providing signals to the microcontroller 20. In particular, the microcontroller 20 send a reference signal to the SP terminal, e.g. a Boolean signal in order to change a logic state. The RP terminal replicates the change of logic state with a delay which is a function of the time constant of the terminal RP which in turn varies dominantly by the capacitance value of the garment sensor 8b.

Further embodiments can provide other example of input stages such as an oscillator for inductive sensors (e.g. elastic twisted yarn as strain sensor), differential pairs (similar to EMG input stage) configured to pick up ECG signals, etc.

The invention claimed is:

1. A system (100) for transmitting signals from a garment (2) having at least one garment sensor (8) to an analysis device (10), said system (100) comprising said garment (2) and a processing unit (1) which is a button (1) of the type attachable to the garment (2) by means of a pin (3) passing through a hole (4) provided in said garment (2), said hole (4) being arranged in a garment coupling portion (5) to be clamped between the head (3a) of said pin (3) and a button coupling surface (6), said button (1) containing at least one integrated circuit (7) for performing analog and digital processing of signals coming from said at least one garment sensor (8), and a wireless module (9) for communicating data between the button (1) and an analysis device (10), wherein said garment coupling portion (5) is provided with at least one conductive trace (11) connected to said at least one garment sensor (8), said at least one conductive trace (11) being arranged on the surface of the garment coupling portion (5), in order to face the button coupling surface (6), and wherein said button coupling surface (6) is provided with at least one electric contact (12) connected to said at least one integrated circuit (7), said at least one electric contact (12) of the button is arranged in order to contact said at least one conductive trace (11) on the surface of said garment coupling portion (5) and is configured to avoid piercing the garment when the button (1) is attached to the garment (2).

2. The system (100) according to claim 1 wherein, the external surface of said at least one electric contact (12) is substantially flat.

3. The system (100) according to claim 1, wherein said at least one electric contact (12) is substantially flush with said button coupling surface (6).

4. The system (100) according to claim 1, wherein said button coupling surface (6) includes a socket (6a) for the engagement of said pin (3) into the button (1), said button coupling surface (6) being provided with a plurality of said electric contacts (12) arranged around said socket (6a).

5. The system (100) according to claim 4, wherein the pin (3), the hole (4) and the socket (6a) are shaped in a such manner that only a univocal alignment is possible between the electric contacts (12) of the button and conductive traces (11) of the garment.

6. The system (100) according to claim 4, wherein the pin (3), the hole (4) and the socket (6a) are shaped in a such manner that when the pin (3) is coupled in the hole (4) and/or in the socket (6a), the pin (3) is constrained in rotation.

7. The system (100) according to claim 1, wherein said button (1) further comprises a battery (15) for power supplying said at least one integrated circuit (7) and the wireless module (9).

8. The system (100) according to claim 7 wherein, the battery (15) is detachable from said button (1).

9. The system (100) according to claim 7 wherein, the battery (15) is contained within the button (1), said battery (15) being rechargeable by an inductive coupling.

10. The system (100) according to claim 1, wherein said button (1) contains at least one button sensor (16) connected to said at least one integrated circuit (7).

11. The system (100) according to claim 10 wherein, said at least one button sensor (16) comprises at least one accelerometer, at least one gyroscope, or a combination thereof.

12. The system (100) according to claim 1, wherein said at least one integrated circuit (7) comprises at least one analog front-end circuit (17) with one or more input stages (18) for performing analog processing of the signals coming from said at least one garment sensor (8) and/or from said at least one button sensor (16).

13. The system (100) according to claim 12 wherein, said at least one integrated circuit (7) comprises at least one A/D converter (19) for digitizing the signals processed by said at least one analog front-end circuit (17) and a microcontroller (20) for performing digital processing of digitized signals and for executing a communication protocol between said wireless module (9) and said analysis device (10).

14. The system (100) according to claim 1, wherein said at least one conducting trace (11) is made of an anti-corrosion material.

15. The system (100) according to claim 1, wherein said garment coupling portion (5) is provided with a plurality of said conducting traces (11) arranged radially around the hole (4) of the garment coupling portion (5).

16. The system (100) according to claim 1, wherein said garment coupling portion (5) comprises an insulating material (13) arranged between the conductive traces (11).

17. The system (100) according to claim 1, wherein said at least one garment sensor (8) comprises a plurality of electrodes (8a-8c) for measuring vital signals, at least one strain sensor (8d), at least one sweat sensor, or a combination thereof.

18. A processing unit (1) for a system (100) according to claim 1, wherein said processing unit comprises said button (1) and said button coupling surface (6) includes a socket (6a) for engagement of the pin (3), wherein.

19. The processing unit according claim 18, wherein said socket (6a) is shaped with a reference portion (14).

20. A garment (2) including the system (100) according to claim 1, wherein said garment coupling portion (5) is provided with one or more of said conductive traces (11) connected to said at least one garment sensor (8), said one or more conductive traces (11) being arranged radially around the hole (4) on the surface.

21. The garment (2) according to claim 20, wherein said hole (4) is shaped with a reference portion (14).

* * * * *